(12) United States Patent
Baskin et al.

(10) Patent No.: US 8,491,924 B2
(45) Date of Patent: Jul. 23, 2013

(54) BIOMATERIAL IMPLANTS

(75) Inventors: Jonathan Baskin, Cleveland, OH (US); Steven J. Eppell, Beachwood, OH (US); Weidong Tong, Warsaw, IN (US)

(73) Assignee: Case Western Reserve University, Cleveland, OH (US)

( * ) Notice: Subject to any disclaimer, the term of this patent is extended or adjusted under 35 U.S.C. 154(b) by 930 days.

(21) Appl. No.: 12/296,988

(22) PCT Filed: Apr. 13, 2007

(86) PCT No.: PCT/US2007/066614
§ 371 (c)(1),
(2), (4) Date: Aug. 3, 2009

(87) PCT Pub. No.: WO2007/121345
PCT Pub. Date: Oct. 25, 2007

(65) Prior Publication Data
US 2010/0021520 A1  Jan. 28, 2010

Related U.S. Application Data

(60) Provisional application No. 60/791,795, filed on Apr. 13, 2006.

(51) Int. Cl.
*A61F 2/00* (2006.01)
*A61F 13/00* (2006.01)

(52) U.S. Cl.
USPC .......................................... 424/422; 424/423

(58) Field of Classification Search
None
See application file for complete search history.

(56) References Cited

U.S. PATENT DOCUMENTS

| 4,971,954 | A  | * | 11/1990 | Brodsky et al. ............... 424/422 |
| 5,320,844 | A  |   | 6/1994  | Liu |
| 6,887,272 | B2 |   | 5/2005  | Shinomiya et al. |
| 7,514,249 | B2 | * | 4/2009  | Gower et al. ............... 435/174 |
| 2005/0272153 | A1 | | 12/2005 | Xuenong et al. |

OTHER PUBLICATIONS

Itoh et al., "Development of an Artificial vertebral body using a novel biomaterial, hydroxyapatite/collagen composite ", Biomaterials 23 (2002),3919-3926.
Itoh et al., "Implantation Study of a Novel Hydroxyapatite/Collagen (Hap/Col) Composite into Weight-Bearing Sites of Dogs", J Biomed Mater Res (Appl Biomater) 63: 207-515, 2002.
Itoh et al., "Development of a novel biomaterial, hydroxyapatite/collagen (Hap/Col) composite for medical use", Bio-Medical Materials and Engineering 15 (2005) 29-41 IOS Press.
Kikuchi et al., "Glutaraldehyde cross-linked hydroxyapatite/collagen self-organized nanocomposites", Biomaterial 25 (2004) 63-69.

* cited by examiner

*Primary Examiner* — Debbie K Ware
(74) *Attorney, Agent, or Firm* — Tarolli, Sundheim, Covell & Tummino LLP

(57) ABSTRACT

A biomaterial implant includes a mineralized collagen fibril scaffold. The collagen fibrils are formed from type I collagen monomers and display native-D band periodicity. The implant has load bearing capabilities and can be resorbed when implanted in a mammal's body.

17 Claims, 11 Drawing Sheets

BIOMATERIAL IMPLANTS

RELATED APPLICATION

This application claims priority from U.S. Provisional Application No. 60/791,795, filed Apr. 13, 2006, the subject matter which is incorporated herein by reference.

FIELD OF THE INVENTION

The present invention relates to biomaterial implants, and particularly relates to methods of producing biomaterial implants that can be used as tissue replacement materials.

BACKGROUND

Hard tissue, such as natural bone, comprises collagen and inorganic calcium phosphate, particularly biological apatite. Bone contains about 60% to 75% by weight of biological apatite and tooth contains more than 98% by weight of biological apatite. Biological apatite is a naturally occurring calcium apatite-type material, which is formed in the body by precipitation from body fluids. Biological apatite has a structure, which is similar to pure carbonated apatite, but contains some substitute ions for the calcium, phosphate and carbonate ions. Synthetically produced precipitated hydroxyapatite is typically more similar to biological apatite than are the hydroxyapatite ceramics.

Collagen can be mineralized by calcium phosphate minerals by inducing the precipitation of calcium phosphate in a collagen slurry. Several patents have disclosed methods of preparation of mineralized collagen by precipitation of calcium phosphate.

For example, U.S. Pat. No. 5,320,844 discloses a mineralized collagen composite material produced by quickly adding a soluble calcium ion-containing solution and a phosphate ion-containing solution into a collagen slurry. The patent further discloses that the slurry is vigorously stirred while maintaining it at a basic pH to thereby induce the mineralization of the collagen. The mineralized collagen is disclosed as being recovered by solid-liquid separation and is then dried.

SUMMARY OF THE INVENTION

The present invention relates to a biomaterial implant that comprises a mineralized collagen fibril scaffold. The collagen fibrils of the scaffold can be formed from type I collagen monomers and display native-D banding periodicity. The biomaterial implant can have load bearing capabilities and be replaced with native bone via normal bone remodeling when implanted in a mammal's body.

In an aspect of the invention, the collagen fibrils can have an average diameter of about 30 nm to about 130 nm. The collagen fibrils can define a plurality of gaps in the scaffold. The gaps can have an average volume of about 50 $nm^3$ to about 250 $nm^3$.

In another aspect of the invention, the collagen fibril scaffold can be mineralized with at least one of nanoscale mineralite, calcium phosphate based mineralite, apatitic mineralite, carbonated apatite, or substituted carbonated apatite. In one example, the mineralite can comprise carbonated apatite.

The mineralites can be interdigitated between the collagen fibrils such that the mineralites are resistant hydrolysis when implanted in the mammal. The mineralites can also have a calcium to phosphorous ratio (Ca/P) of about 1.4 to about 1.8 and an average particle size of about 25 $nm^3$ to about 150 $nm^3$.

In a further aspect, the biomaterial implant can be osseoconductive and resistant to hyrodrolysis when implanted in a mammal. The biomaterial implant prior to implantation can have a modulus of about 500 MPa to about 20 GPa, e.g., about 5 GPa to about 20 GPa.

In another aspect of the invention, the biomaterial implant can comprise at least one bioactive molecule, growth factor, or bone morphogenic protein. The biomaterial implant can be doped with bioactive molecule, growth factor, or bone morphogenic protein. Optionally, the bioactive molecule, growth factor, or bone morphogenic protein can be interdigitated between collagen molecules within the collagen fibrils to allow for slow diffusion of the bioactive molecule, growth factor, or bone morphogenic protein into the extracellular milieu as the biomaterial implant is resorbed. In one example, the bioactive molecule, growth factor, or bone morphogenic protein can comprise recombinant human hone morphogenic protein.

In yet another aspect of the invention, the mineralized collagen fibril scaffold can be at least partially cross-linked with a cross-linking agent. The cross-linking agent can include a D-ribose solution.

The present invention also relates to a method of forming a biomaterial implant. The method comprises forming a collagen fibril scaffold wherein the collagen fibrils display native-D banding periodicity. The collagen fibril scaffold can be mineralized so that the collagen fibril scaffold has a mineral composition similar to native bone. The mineralized collagen fibril can be then be densified. The densified mineralized collagen fibril scaffold can have load bearing capabilities and be replaced with native bone via normal bone remodeling when implanted in a mammal's body.

In an aspect of the method, the collagen fibril scaffold can be formed by incubating a type I collagen monomer in a buffered saline solution to produce a hydrogel. The collagen fibrils so formed can have an average diameter of about 30 nm to about 130 nm and define a plurality of gaps in the scaffold. The gaps can have an average volume of about 50 $nm^3$ to about 250 $nm^3$.

In another aspect of the method, the collagen fibril scaffold can be mineralized by immersing the collagen fibril scaffold in a mineralization solution. The mineralization solution can have pH that is higher than the pH of the buffered saline solution. The mineralization solution can include, for example, calcium chloride dihydrate, sodium bicarbonate, potassium chloride, and potassium phosphate dibasic anhydrous. The mineralized collagen fibril scaffold can have a calcium to phosphorous ratio (Ca/P) of about 1.4 to about 1.8.

In a further aspect of the method, the mineralized collagen fibril scaffold can be densified by uniaxially pressing the mineralized collagen fibril scaffold. The mineralized collagen fibril scaffold can also be densified by cold isostatic pressing the mineralized collagen fibril scaffold.

In a still further aspect of the method the at least one of bioactive molecule, growth factors, or bone morphogenic proteins can be interdigitated between collagen fiber and the collagen fibril can be at least partially cross-linked.

The present invention also relates to a method of treating a bone injury or defect in a subject. The method includes administering to the injury or defect of the subject a biomaterial implant. The biomaterial implant includes a mineralized collagen fibril scaffold. The collagen fibrils are formed from type I collagen monomers and display native-D banding periodicity. The implant has load bearing capabilities and is replaced with native bone via the normal bone remodeling when administered to the injury or defect. The injury or defect can comprise at least one of a craniomaxillofacial injury or defect, a spine injury or defect, an appendicular injury or defect, or a pan-skeletal injury or defect.

In an aspect of the invention, the biomaterial implant can be shaped with presses that are preshaped to the particular injury or defect prior to implantation. The biomaterial implant can also be machined prior to administration.

In a further aspect, the collagen fibrils can have an average diameter of about 30 nm to about 130 nm. The biomaterial implant can be osteoconductive and resistant to hyrodrolysis when implanted in the subject. The collagen fibril scaffold can be mineralized with at least one of nanoscale mineralite, calcium phosphate based mineralite, apatitic mineralites, carbonated apatite, or substituted carbonated apatites. The mineralite can have a calcium to phosphorous ratio (Ca/P) of about 1.4 to about 1.8.

In another aspect, the biomaterial implant can include at least one of bioactive molecule, growth factor, or bone morphogenic protein interdigitated between collagen molecules within the collagen fibrils. The mineralized collagen fibril scaffold can be at least partially cross-linked with a cross-linking agent.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Figure 1:
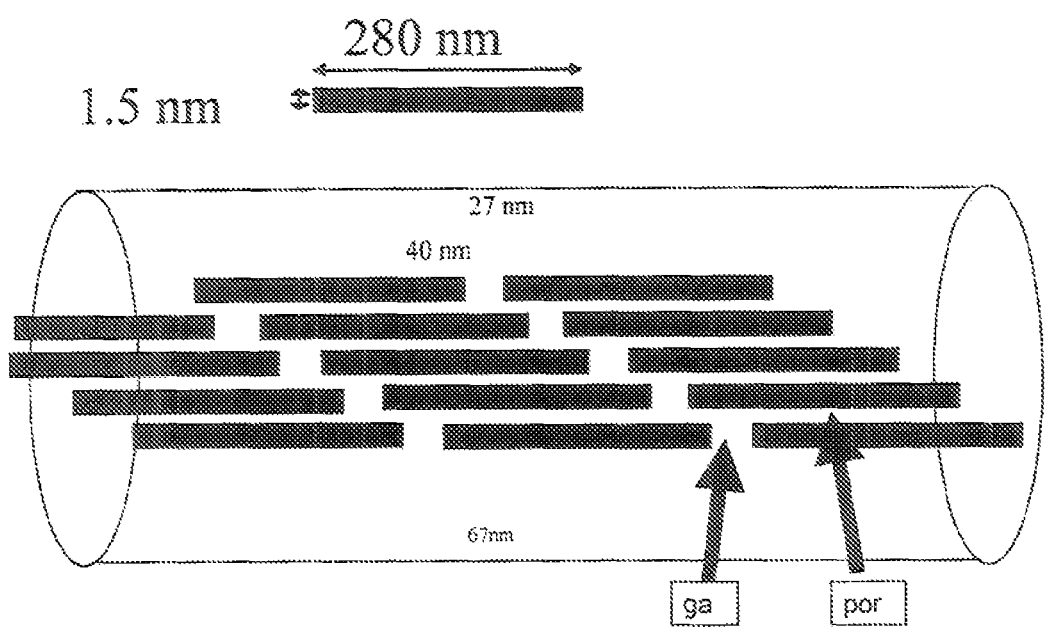
FIG. 1 is a schematic illustration of a collagen fibril in accordance with an aspect of the invention.

The present invention relates to a biomaterial implant that includes a biomimetic material that is osteoconductive and capable of osseointegration after implantation. The biomaterial implant can be used as a load-bearing bone substitute to treat bone injuries and/or bone defects in a mammalian subject. Examples of uses of the biomaterial implant can include: craniomaxillofacial surgery applications, such as dental applications (e.g., alveolar procedures, implant surgery (i.e., sinus lift)), orthognathic surgery (i.e., used to stabilize the jaw in skeletal advancement) and head and neck/facial plastic and reconstructive surgery (e.g., cranioplasty, skeletal (facial) augmentation, post traumatic reconstructive work in the craniofacial skeleton (i.e., orbital reconstruction)), and post cancer treatment reconstruction (i.e., mandibular defects); spine surgery, such a fusion, anterior, and posterior spine surgery and spinal traum or oncological surgery; appendicular skeleton applications, such as the treatment of limb defects secondary to trauma, oncological treatment, or congenital disorders, joint surgery either alone or in combination with other hardware (e.g., hip replacement), and limb lengthening surgery; and plastic and reconstructive surgery, such as pan-skeletal treatment for defects that result from trauma or infectious processes. The biomaterial implant can also be used in the fabrication of fixation devices, such as bone screws.

The biomaterial implant can have structural integrity to bear a load in parts of the skeleton once implanted and interact with osteoclasts allowing for resorption via the normal bone remodeling cycle as opposed to hydrolysis followed by an inflammation related foreign body response. By normal bone remodeling cycle, it is meant that the biomaterial implant is first resorbed by osteoclasts, creating shallow resorption pits in the biomaterial. Osteoblasts then deposit compact bone within the resorption pits to replace the resorbed implant material. The resorption can occur at a site and patient specific rate to allow for osteoblastic bone production tied to resorption rate. The rate or resorption of the biomaterial implant can be tailored to allow for rapid resorption without loss structural integrity and without inciting an inflammatory response beyond that expected normally after a surgical procedure.

The biomaterial implant in accordance with the present invention comprises biomimetic nano-composite that includes a mineralized collagen fibril scaffold. The collagen fibril scaffold can comprise type I collagen fibrils that display native D-banding periodicity. Collagen is readily employed because its degradation products integrate with osteoclastic activity and the normal bone remodeling cycle. Other resorbable polymeric materials that have properties similar to collagen can also be employed. Such other materials can potentially include synthetic alpha polyester, such as polylactic acid polymers, polyglycolic acid polymers and or copolymers and blends thereof. However, these are not expected to be as advantageous as collagen because they are not replaced with bone via a cellular remodeling process.

The collagen fibril scaffold can include gap spaces that when mineralized result in a nanophase composite similar to native bone on the sub-micron scale. One example of longitudinally extending collagen fibril scaffold is schematically illustrated in FIG. 1. FIG. 1 shows that the gap spaces can be about 50 nm$^3$ to about 250 nm$^3$ in size, for instance, about 100 nm$^3$ (e.g., about 10 nm×about 10 nm×1 nm) in size. The gaps can be spaced axially about 100 nm to about 300 nm apart (e.g., about 280 nm apart), radially about 0.5 nm to about 10 nm apart (e.g., about 1.5 nm apart), and staggered away from the center of the fibril to its perimeter by about 25 nm to about 100 nm (e.g., about 67 nm) along the axial direction.

The frequency of the D-banding of the collagen fibril scaffold is such that nanoscale mineralites can be interdigitated within the collagen fibril scaffold and sterically hindered so that the mineralites do not diffuse away from biomaterial implant when the biomaterial implant is exposed to aqueous solutions. In one example, the frequency banding can have a period of about 50 nm to about 100 nm. In another example, the frequency banding can have a period of about 60 nm to about 75 nm. A frequency banding of about 50 nm to about 100 nm (e.g., about 60 nm to about 75 nm) indicates that the collagen fibril scaffold has an internal void spaces necessary to achieve biomimetically distributed mineral within the collagen fibril scaffold.

The collagen fibrils of the scaffold can also have and average diameter of about 30 nm to about 130 nm. By way of example, the collagen fibrils can have an average diameter of about 50 nm to about 100 nm (e.g., 75 nm).

The minerals or mineralites provided in the collagen fibril scaffold of the composite can include minerals typically found in natural bone. These minerals can include calcium phosphate based minerals, such as nano-scale mineralite, carbonated nano-apatite, calcium phosphate based mineralite, tri-calcium phosphate, octa-calcium phosphate, calcium deficient apatite, amorphous calcium phosphate, hydroxyapatite, substitute apatite, carbonated apatite-like minerals, highly substituted carbonated apatites or a mixture thereof. In one example, the minerals provided in the collagen fibril scaffold comprise nanoscale carbonated apatite.

The concentration or density of mineralization of the collagen fibril scaffold can be that density of mineralization which is similar to that of natural bone. The desired mineral density can be determined by comparison with a standard. Alternatively, the desired mineral density or concentration can be determined by a non-invasive bone mineral density assessment of the patient and then selection of a material that matched the patients' native mineral concentration.

The density of the mineralization of the biomaterial implant need not be uniform across the biomaterial implant and can depend on the specific therapeutic application. For example, the density of mineralization of an outer region of the biomaterial implant can be less than the density of mineralization of an inner region of the biomaterial implant. A less densely mineralized outer region can permit more rapid natural bone in growth and a more densely mineralized inner region can provide greater and more long-term load bearing capacities. In other examples, the mineral density of the inner region of the biomaterial implant may be less dense than the mineral density of the outer region of the biomaterial implant.

The mineralization content of the collagen fibril scaffold can be quantified by looking at the size and shape of the mineral as well as its elemental composition and atomic crystallinity. These studies have been performed predominantly on powders isolated from mineralized gels using hydrazine extraction. The mineral powders can be dispersed in ethanol and imaged by, for example, atomic force microscopy (AFM). Mineralization of the collagen fibril scaffold can also be measured using Energy Dispersive Absorption of X-rays (EDAX) to assay the chemical composition of mineral within the collagen.

It has been shown that a structurally biomimetic bone substitute needs to contain apatitic mineralites that are, for example, about 1 nm×about 10 nm×about 10 nm. Nature meets this design constraint by templating mineralization using collagen fibrils. The nanoscale voids within a self-assembled native collagen fibril limits the size to which the mineralites can easily grow and entraps the mineralites so they do not diffuse away from the collagen fibrils. In fabricating the composite material, this process has been essentially replicated.

The size of the minerals formed in collagen fibril scaffold can correspond to that of lightly mineralized collagen. For example, the size of the minerals can be about 24 nm$^3$ to about 100 nm$^3$ (e.g., about 9 nm±about 3 nm×6 nm±about 2 nm×2±about 1 nm). This corresponds to the mineralization of about 1 to about 3 month old bovine cow bone. If the collagen fibril scaffold is more heavily mineralized, the size of the minerals can be, for example, about 12 nm×10 nm×0.6 nm. This mineralization corresponds to mature bovine cow bone.

The ratio of calcium to phosphorous of the mineralization material can also be selected. One example of a target calcium to phosphorus ratio of biomaterial implant as determined by EDAX is about 1.66±0.33 (corresponding to an apatitic composition within the conventional error of the EDAX measurement). It will be appreciated that the target Ca/P ratio need not necessarily be about 1.66. A higher or lower Ca/P ratio can also is also acceptable as long as it is similar to natural bone, which has a Ca/P ration of about 1.4 to about 1.8. In addition, the minerals in the material may also contain carbonate groups, like natural bone, and FTIR (infrared spectroscopy) or Nuclear Magnetic Resonance (NMR) may be employed to detect these.

The mineralization of the collagen fibril structure (and of the biomaterial implant) can further be measured using x-ray diffraction (XRD) spectroscopy. One example of a target XRD spectra shows slightly broadened 002 and 310 peaks along with a single broad peak around 32 degrees corresponding to a substantially broadened 211, 112, 300 set of peaks.

This is the typical spectra obtained with the very small highly substituted apatites previously isolated from bone samples.

The biomaterial implants of the present invention can also incorporate bioactive agents or drugs, such as antibiotics, bone morphogenetic proteins (e.g., recombinant human bone morphogenic protein 2 (rhBMP2)), other bone growth factors, skin growth factors or anti-scarring agents, such as transforming growth factor-Beta. In such case, the drugs can be doped or interdigitated in between collagen molecules within the fibril scaffold.

In order to enhance the mechanical strength of the collagen fibril scaffolds, the collagen fibril scaffolds can be cross-linked using various sugar derivatives, such as glyoxal, D-ribose, or genipin. Other cross-linking agents, such as glutaraldehyde, can also be used. Concentrations of the crosslinking agent as well as time and temperature used for crosslinking can be varied to obtain the optimal results.

In an aspect of the invention, the biomaterial implant can have a dry modulus of about 500 MPa to about 20 Gpa. In another aspect, the modulus of the biomaterial implant can be about 10 Gpa to about 20 Gpa, which is typical for cortical bone. The wet modulus of the biomaterial implant can be about 5.0 Mpa to about 10.0 Mpa (e.g. about 6.0 MPa). The biomaterial implant can have a shape similar to the shape of the defect or injury being treated and/or repaired. For example, biomaterial implants in accordance with the present used to repair bone deficits can have a shape of the deficit to which the implant is to be applied. In other applications where the biomaterial implant is used as a resorbable load bearding fixation device the biomaterial implant can have the shape of a bone screw, such a helical bone screw.

Figure 2:
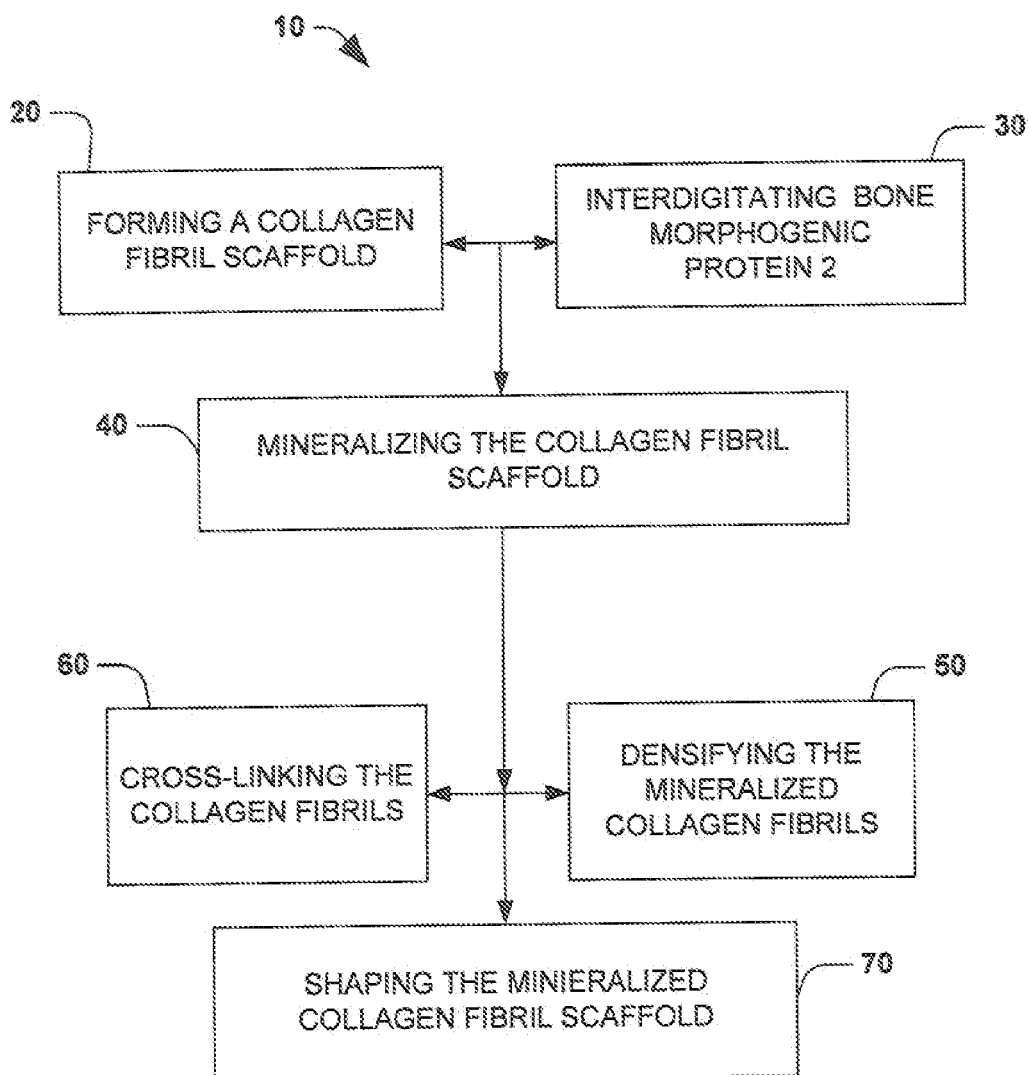
FIG. 2 is a flow diagram illustrating one method of forming a biomaterial implant in accordance with an aspect of the invention.

The biomaterial implant of present invention can be synthesized using a multi-step process. FIG. 2 illustrates a schematic flow diagram of a synthetic method 10 of synthesizing a biomaterial implant in accordance with an aspect of the invention.

In the method, at 20, a collagen fibril scaffold comprising collagen fibrils having a diameter of about 30 nm to about 130 nm (e.g., about 75 nm diameter) is formed from type I collagen monomers. The type I collagen monomers can include, for example, purified bovine collagen. An example of a stock of collagen monomers that can be used is lightly pepsin digested acid solubilized type I calf skin collagen (obtained from Cohesion corp. as VITROGEN). Another example of stock of collagen monomers can be obtained from Inamed Biomaterials, under the trade name PURECOL. The collagen, fibrils can be formed from the collagen monomers so that they display native type D-banding periodicity (Hodge-Petruska model). The native D-banding periodicity can have a frequency banding of about 50 nm to about 100 nm (e.g., about 60 nm to about 75 nm).

One example of a method of forming collagen fibrils displaying D-banding periodicity from the collagen monomers includes combining a stock solution with the collagen monomers and simultaneously neutralizing and warming the collagen monomers. Any suitable buffer can used as stock solution. Such buffers can include, for example, phosphate buffered saline or TES. An example of one buffer that has been used is prepared by measuring out about 750 ml of purified water and then adding to the water with stirring and gentle heating (the solution is not brought to a boil) about 6.45 g NaCl, about 6.88 g TES, and about 4.26 g $NaHPO_4$. About 1 N HCL can be added to the stock, solution to bring the pH to about 7.2. The stock solution can then be topped off with purified water to bring the solution to 1 L.

About 15 ml of the stock solution can be measured and then heated to about 36.5° C. While at about 36.5° C., 1 ml of the collagen source (equivalent to about 3 mg of collagen) can be added to the heated solution and then incubated for about 24 hours. The incubated solution can form a gel that comprises the collagen fibrils that display native type D-banding periodicity.

It was observed that in preparation of the collagen fibrils, the addition of collagen monomers to the buffer tends drive the buffer toward acidic pH. If the pH drops substantially below 7.0, fibrils will not form. Thus, a relatively strong buffer is needed if one wishes to obtain a high initial collagen fibril.

It will be appreciated that the present invention is not limited to this particular method and that other methods can be employed to form collagen fibrils displaying D-banding periodicity from the collagen monomers. These other methods can include conventional methods typically used for forming collagen fibrils displaying D-banding periodicity.

Substantially simultaneous with 20, at 30, recombinant human bone morphogenic protein 2 (rhBMP2), or another bioactive factor, can be interdigitated between collagen molecules of the collagen fibril scaffold. RhBMP2 is a known as a potent osteoinductive material. Interdigitating rhBMP2 between collagen molecules renders it more effective by allowing for slow release of the rhBMP2 into the extracellular matrix as the implanted biomaterial is remodeled and replaced with bone. This increases the material's osteoinductivity by improving penetration of the rhBMP2 into the material and prolonging its effect while reducing the necessary quantity and cost.

The BMP2 can be placed in solution with the collagen monomers so that when the monomers assemble into fibrils, some of the gap spaces will be filled with BMP2. BMP2 that locates in places other than a future gap space will likely prevent accumulation of further collagen monomers and stop fibril growth. Thus, the final location of BMP2 in assembled fibrils is predominantly in the gap spaces. The fibril provides substantial steric hindrance to any enzymes or other molecules with characteristic dimensions larger than a few Angstroms from gaining access to the BMP2. Thus, the BMP2 can remain stable until the fibril is degraded during the remodeling process. Since BMPs in general are used naturally as growth factors during remodeling, it is expected that the cocktail of enzymes released by resorbing osteoclasts is unlikely to break down the BMP2.

At 40, the collagen fibril scaffold can be mineralized with minerals typically found in natural bone so that the minerals are provided in the gaps and pore regions within the fibrils. In one example, nanoscale carbonated apatites are formed in the hole zones and pore regions within the fibrils using a metastable mineralization solution of calcium phoshphate (Ca—P) buffered to a pH and temperature to promote mineralization. The pH and temperature of the mineralization solution can be for example, respectively, about 8.0 to about 8.4 and about 36.5° C. By way of example, the mineralization solution can include sodium carbonate ($NaHCO_3$), potassium chloride (KCl), sodium chloride (NaCl), potassium phosphate dibasic anhydrous ($K_2HPO_4$), calcium chloride dihydrate ($CaCl_2.H_2O$), deionized water, and TES buffer.

In another aspect, since the mineralizing solution results in a metastable state, continuous addition of ions to the solution can be used to maintain mineralization over extended periods. For example, two solutions: one with $CaCl_2$ and NaCl, the other with $K_2HPO_4$ and $NaHCO_3$ can be placed in separate burettes and dispensed via a computer controlled titrator. The system utilizes pH (monitored with a glass/Ag/AgCl electrode) as the control parameter. As apatitic mineralites form, basic carbonate groups become incorporated in the mineral precipitating out of solution resulting in a drop in pH. By detecting small drops (about 0.003 units) in pH and then simultaneously releasing the two solutions, the ionic concentration can be kept constant thus maintaining a constant molar composition of the reactants. $CO_2$ can be excluded from the solutions by bubbling $N_2$ gas prior to and during mineralization. The time of mineralization can be varied to yield a material that is most biomimetic with the best mechanical properties.

At 50, before, during, and/or after mineralization, the mineralized fibrils can be densified so that the mineralized collagen fibril scaffold has a strength and modulus that closely approximates bone. In one aspect, the density of the mineralized collagen fibril scaffold can be increased by mechanically pressing the mineralized collagen fibrils. The mineralized collagen fibrils can be mechanically pressed by placing the mineralized collagen fibril scaffold in a uniaxial press and pressing the mineralized collagen fibrils at a pressure and time period effective to increase the density mineralized collagen scaffold. By way of example, the mineralized collagen fibril scaffold can be placed in a uniaxial press and pressed at a pressure of about 400 kPa to about 600 kPa (e.g., about 500 kPA) for about 12 to about 36 hours (e.g., about 24 hours). After mechanically pressing mechanical pressing, the mineralized collagen fibril scaffold can be dehydrated to yield the densified biomaterial implant.

Optionally, the uniaxially pressed biomaterial implant can be subjected to cold isostatic pressing (CIP) at about 150 MPa to about 250 Mpa (e.g., about 200 Mpa) for variable lengths of time (e.g., about 5 hours). For example, the biomaterial implant can be cold isotatic pressed about 200 MPa for about 5 hours in an Innovare Hydrostatic Extrusion Rig utilizing peanut oil as a pressure medium. The rational for this pressure and time is supported by (Lewandowski, J. J., Lowhaphandu, P., "Effects of hydrostatic pressure on mechanical behavior and deformation processing of materials," International Materials Reviews, 1998, 43(4), pp. 145-187.)

Further, the implants can be perforated in various orientations to allow for better fibrovascular ingrowth following implantation. Additionally, the presses used for cold isostatic pressing and/or uniaxially pressing the biomaterial implant can be preshaped to a particular defect for custom fabrication of the implants.

At 60, following (or before) mineralization, and/or before, during, after densification, the collagen fibrils can be cross-linked. Cross-linking of the collagen fibers can be performed using various sugar derivatives, such as glyoxal, D-ribose, or genipin though several others agents (such as glutaraldehyde) are also good crosslinking candidates. Concentrations of the crosslinking agent as well as time of crosslinking can be varied to obtain the optimal results.

At 70, before, during or following densification and/or cross-linking, the mineralized collagen fibril scaffold can be shaped to a desired configuration for implantation in the subject being treated. In one aspect, the mineralized collagen fibril scaffold can be shaped by pressing the mineralized collagen fibril scaffold in a press that is preshaped to the particular injury or defect. The press can be the same press that is used during the densification of the mineralized collagen fibril scaffold.

In another aspect, the mineralized collagen fibril scaffold can be machined after densification to a shape that can be used for treating the injury or defect. By way of example, the densified mineralized collagen fibril can be machined with hand-held grinder to the desired shape for the specific application prior to implantation in the mammal.

It is to be understood and appreciated that the illustrated steps may occur in different orders and/or concurrently with other actions. For example, densification may occur before, after, and/or during cross-linking of the biomaterial implant. Moreover, not all features illustrated in FIG. 2 may be required to implement a method.

EXAMPLE

Below is a description of the design, manufacture, and implantation of an example of a biomaterial implant in accordance with the present invention. The fabrication is described followed by physico-chemical characterization and in-vitro cytocompatibility studies. Finally a pilot study in rats is described and implant efficacy is evaluated using mechanical studies Methods Implant Preparation Briefly, implants were formed in a three step process involving: formation of collagen fibril gel, mineralization of the gel, and pressing of the gel into a surgically useful form. Each of these steps is described in more detail below. All steps were carried out using standard aseptic techniques.

Reconstitution of Collagen Fibrils

Highly purified lightly pepsin-solubilized bovine dermal collagen (Vitrogen from Cohesion, Palo Alto) was diluted to about 0.2 mg/ml in phosphate buffered saline solution (PBS, Sigma) at pH 7.4 and 36.5° C., and incubated for 24 hours. This produced visible hydrogels that could be removed intact from their beakers using a forceps.

Mineralization of Collagen Fibrils

Mineralization of collagen fibrils was carried out in a metastable MSBF (Modified Simulated Bone Fluid). The MSBF was prepared by adding the following chemicals to 750 ml deionized water:

200 ml TES (N-Tris(hydroxymethyl)methyl-2-aminoethanesulfonic Acid, F.W. 229.2) buffer 100 mM. This solution is prepared by adding 12.1 g TES white crystals to 1 L deionized water and pH adjusted to 7.4.

8 g NaCL (Sodium Chloride, F.W. 58.44)

0.352 g $NaHCO_3$ (Sodium Bicarbonate, F.W. 84.01)

0.224 g KCl (Potassium Chloride, F.W. 74.55)

0.174 g $K_2HPO_4$ (Potassium Phosphate Dibasic Anhydrous, F.W. 174.18)

0.368 g $CaCl_2.H_2O$ (Calcium Chloride Dihydrate, F.W. 147.02)

Additional deionized water to make 1 L of fluid

The solution was adjusted to pH 8.2 just prior to mineralization by adding 1 M NaOH. Gels were incubated at 36.5° C. for 24 hours.

Mechanical Pressing

Mineralized gels were rinsed in pure ethanol several times then placed into ABS plastic presses designed to create a shape that conformed to the critical size defect in a rat mandible (circular discs about 5 mm in diameter and about 2 mm thick). Sapphire flats placed on either side of the gel provide uniform surface geometry. The press body had small radial holes which allowed water to be extruded from the gel during mechanical dehydration. The material was pressed using 347 KPa for 24 h.

Physico-Chemical Analysis of Implant Material

Characterization of Collagen Phase

We intended to manufacture nanoapatites interdigitated within collagen fibrils by templating mineralization within a native D-banded collagen fibril. To assay whether the first collagen fibril formation step described above produced such fibrils, we used uranyl acetate negative staining of these gels followed by transmission electron microscopy imaging.

Staining of Collagen Fibrils in Preparation for TEM Imaging

Fibrils were deposited on a carbon film supported by a copper grid and rinsed with millipore water three times. The collagen fibrils were subsequently stained with 1% uranyl acetate (pH 4.3) then dried overnight in a clean container before imaging by transmission electron microscopy (JEOL 1200 EX.).

Characterization of Mineral Phase

To measure sizes of mineral components too small to be easily seen by TEM, we used atomic force microscopy (AFM). To ensure the surfaces imaged by AFM contained only the mineral phase of our nanocomposite, we performed a hydrazine extraction on the mineralized gels.

Hydrazine Extraction of Mineralized Collagen

Mineralized collagen was washed extensively using 100% ethanol. Four cycles of the following two steps were used. First, the gels were dispersed in anhydrous hydrazine (Sigma) at 4° C. for 24 hours (1.5 mg collagen/1 ml hydrazine). Second, the solution was centrifuged at 14,000 g for half an hour and the supernatant was extracted for disposal. Hydrazine extracted mineralites were subsequently washed four times at 4° C. by adding 100% ethanol, centrifuging, and extracting the supernatant. The final product was obtained by evaporating the ethanol in the centrifuge tube in a 25 ml container covered by filter paper. A control sample was prepared using all the steps of fibril formation, mineralization, and hydrazine extraction but without collagen added.

AFM Sample Preparation and Imaging

AFM substrates were prepared on freshly cleaved mica (Laboratory High Quality Mica, Asheville-Schoonmaker Mica Co.). Dry powders of the isolated synthetic apatites were suspended in 100% ethanol in a glass vial sealed using Parafilm. To ensure powder dispersion in the ethanol, vials were sonicated for 5 minutes at 4° C. While the vials were magnified, a 5 µl aliquot was removed from the center of the glass vial, deposited on the mica and placed in a covered petri dish overnight. The control sample was prepared under the same condition.

Samples were imaged in air with an atomic force microscope (Nanoscope III Multimode, Digital Instruments, Santa Barbara, Calif.) operated in tapping mode using a silicon cantilever (Nominal spring constant: 42 N/m, Nanosensor, Wetzlar-Blankenfeld, Germany). Operation of an AFM in general and tapping mode in particular have been well described elsewhere. The precision of our measurements was limited by digitization of the data to about 0.01 nm for thickness and 1 nm for length and width. Noise in the thickness measurements was about 0.2 nm rms. To account for the tip dilation artifact, probe tips were measured using a Nioprobe standard (Electron Microscopy Sciences, F.T. Washington, Pa.) and a blind reconstruction algorithm used to reconstruct the probe shape. Morphological erosion was then performed prior to measuring mineralite sizes from the AFM data.

To examine how closely our mineralite crystallinity matched with mineralites isolated from mammalian bone, we performed X-ray diffraction on the hydrazine extracted mineralites.

X-Ray Diffraction (XRD) of the Synthetic Apatites

/2θ diffractometer scans of synthetic mineralites were recorded on a Phillips PN 3550 diffractometer (Ni-filtered Cu Kα radiation). The data was collected at 2θ increments of 0.05 degrees with a 30 s counting time at room temperature between 3°-60° (2θ).

Cytocompatability of Implant Material

To see if our material was cytocompatible with cell types found in bone, we performed an in-vitro assay. This assay was done using mineralized gels that had not yet been pressed.

In Vitro Cytocompatibility Studies

A coculture of mesenchymal support cells and hematopoietic progenitor cells was utilized. Frozen cells from the ST2 mesenchymal cell line (Riken cell bank) were thawed and suspended in Gibco α-MEM supplemented with 10% heat inactivated fetal bovine serum (Hyclone, Logan, Utah), 2 mM L-glutamine (Mediatech, Holly Hill, Fla.), 100 U/ml penicillin (Mediatech), and 100 µL/mL streptomycin (Mediatech). The cell suspension was plated in 100 mm Falcon culture dishes and incubated at 37° C. and 5% CO2. After confluence was reached, the ST2 cells were lifted from their plates with pronase (Sigma-Aldrich) and plated onto 3 different substrates: collagen scaffold (unmineralized), sintered hydroxyapatite, and the nanocomposite at a density of 1700 cells/cm2. Cultures were maintained at 37° C. and 5% $CO_2$.

The next day, 6 to 14 week-old mice (strain C57BL6) were asphyxiated by CO2. The mice were treated in accordance with the National Institutes of Health guide for the Care and Use of Laboratory Animals. Afterwards the spleens were dissected from the mice and the contents enucleated and placed in basal MEM (Gibco) supplemented with 10% FBS, 2 mM L-glutamine, non-essential amino acids (Mediatech), 100 L/ml penicillin, and 100 µL/mL streptomycin. Erythrocytes were eliminated by adding 0.83% ammonium chloride to the suspension. The remaining cells were plated onto the 3 different substrates at a density of 520,000 cells/cm$^2$. Cells were also plated on a few samples of elephant ivory as a positive control for osteoclast formation and activation. Supplements including 100 nM dexamethasone (Sigma), 10 nM 1.25 $(OH)_2D_3$ (Biomol), and 50 µg/mL ascorbate (GIBCO) were subsequently added to the cultures. Media and supplements were changed every 3 days. Culture was ended after ten days. Cultures were performed 3 separate times on 3 different sets of substrates.

In-Vivo Assay of Implant Material

Implantation of Nanocomposite in Rat Mandible Critical Sized Defects

This study involves manipulation of the craniofacial tissue on a minimal level. Primitive responses of bone to basic functional craniofacial skeletal manipulations are shared by all mammals. Therefore the rat, as a generic animal model, is considered to be appropriate for this level of hypothesis testing. The purpose of this pilot study was to establish proof of concept and not necessarily to generate statistically significant data. Adult Sprague Dawley rats were divided in four groups with 2 rats in each group—two control groups and two experimental groups. All animals had critical size defects. The control groups included a defect with nothing implanted and a collagen sponge implantation. Experimental groups included implantation with a nanocomposite and a nanocomposite doped with rhBMP2.

The rats were anesthetized with an intraperitoneal injection of a standard anesthetic cocktail composed of ketamine hydrochloride (60 mg/kg) and xylazine (5 mg/kg). Surgery on the mandible commenced when adequacy of the anesthesia had been confirmed. A linear incision was made along the inferior border of the mandible. After the subcutaneous tissues were divided, the masseter muscle was separated from the mandible at its inferior border and the body of the mandible exposed in the subperiosteal plane. A full thickness critical sized defect (5×5 mm) was created in the body of the mandible in all experimental and control animals using a medium speed drill with a daimond burr and copious irrigation.

In group 1, the wound was closed immediately following creation of the critical size defect. The wound of every animal was closed meticulously in two layers using resorbable suture. Special attention was given to closing the periosteal layer so there was complete periosteal coverage of the defect. In group 2, a collagen sponge was placed in the defect. Group 3 had a uniaxially pressed nanocomposite placed into the bony defect. Custom uniaxial presses were designed to enable a precise fit of the implant into the defect. The shape allowed the implant to be wedged into place. The implants were all stable and did not require any other fixation. In group 4 the pressed nanocomposite was doped with rhBMP2 prior to implantation.

Post-operatively, the animals were treated with antibiotics (kefzol), steroids (decadron), and pain medications (buprenorphine). They were housed in an animal facility, initially in individual cages and fed soft diets (ground rat chow) ad lib for the first week. Within the first 7 days, when given the choice, all rats chose a regular diet of rat chow which is what they were fed for the remainder of the study. At 56 days the animals were euthanized by lethal injection (>150 mg/kg of pentobarbital given intraperitoneally). The mandibles were harvested for examination.

Mandibles with critical size defects (no implantation) and those in groups 3 and 4 were split in the midline to create hemimandibles for mechanical studies. The other mandibles were subject to other processing and were not available for mechanical testing. Four point mechanical bend tests were performed on each hemimandible. For each animal the 4-point bend was performed on the operated hemimandible and the unoperated contralateral side. The resulting load and stiffness were then measured and expressed as a ratio of the operated to the unoperated side. In this way, the values were controlled for inter-animal variability.

The animal study was performed with IACUC approval at the animal resource center at Case Medical School.

Figure 3:
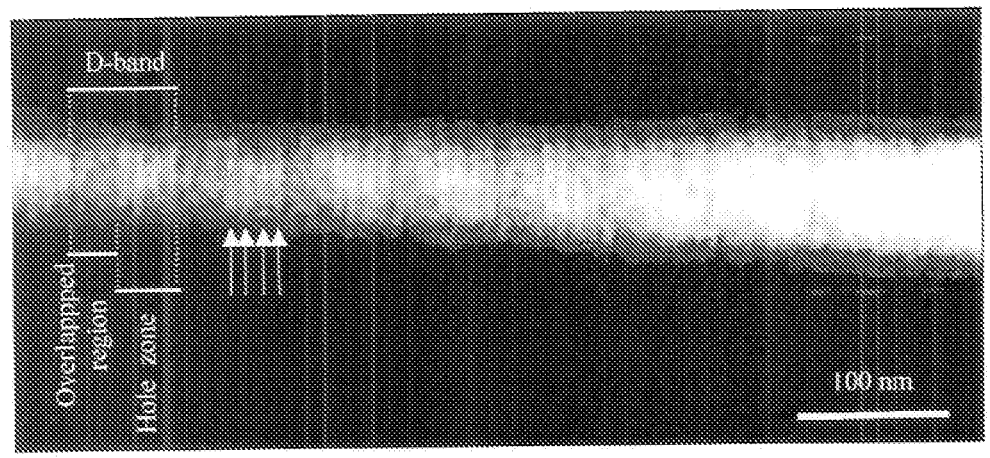
FIG. 3 illustrates a TEM image (inverted) of negatively stained collagen fibril. Banding pattern with 67 nm periodicity (D-period) can be observed along the long axis of the collagen fibril. The hole zone is about 0.6 D in length, and the overlapped region is about 0.4 D in length. Four sub-bands are observed within the hole zone (indicated by vertical white arrows). The picture below the TEM image illustrates the ordering of the collagen molecules within the fibril according to Hodge-Petruska scheme. The head and end of the arrow represent the N- and C-terminals of the collagen molecule. The solid rectangular shapes represent the stain-penetrable hole zones.
Figure 3:
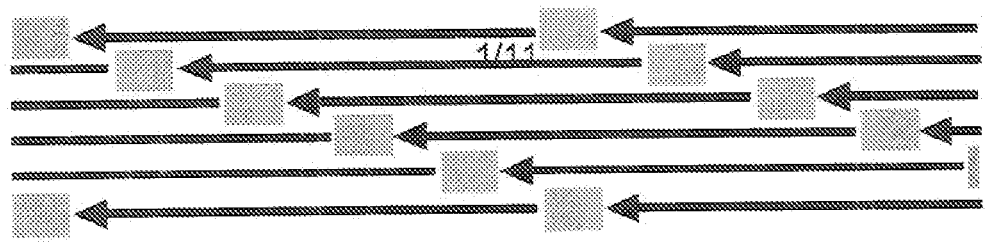
Figure 4:
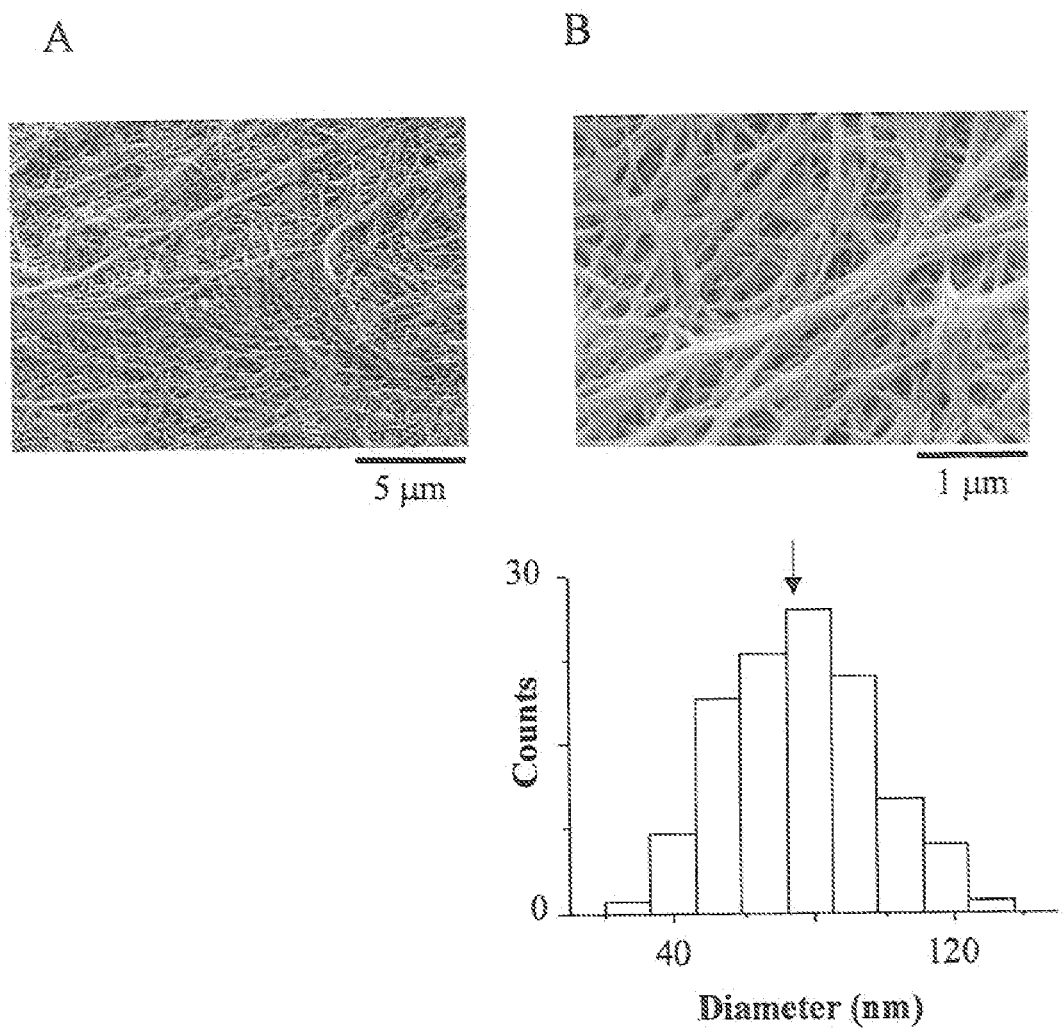
FIG. 4 illustrates SEM images of reconstituted collagen fibrils. (A) At low magnification (×6 k), collagen fibrils entangle together with no apparent ordering of the fibrils. (B) At high magnification, (×30 k), diameters (widths) of the reconstituted collagen fibrils vary to a certain extent. Histogram below the SEM image shows that the diameter ranges from 30 nm to 130 nm, with a mean average of 75±21 nm (n=115).

Physico-Chemical Analysis of Implant Material
Structure and Sizes of Reconstituted Collagen Fibrils FIG. 3 shows a representative TEM image of the negative stained collagen fibril. The image shows alternating bright-dark bands at two distinct spatial periodicities. The lower frequency banding has a period of 67±4 nm. This indicates that our fabrication procedure produces a template having internal void spaces necessary to achieve biomimetically distributed mineral within the collagen phase. The diagram below the TEM image illustrates the ordering of collagen molecules (long arrows) within the fibril and the stain-penetrable hole zones according to Hodge-Petruska scheme. An SEM image at low magnification shows that the fibrils show no apparent ordering and are at least 15 μm long between branching points. Fibril diameters measured from the SEM images at high magnification (×30 k) (FIG. 4) are 75±21 nm.

Characterization of Mineralized Collagen Fibrils

Figure 5:
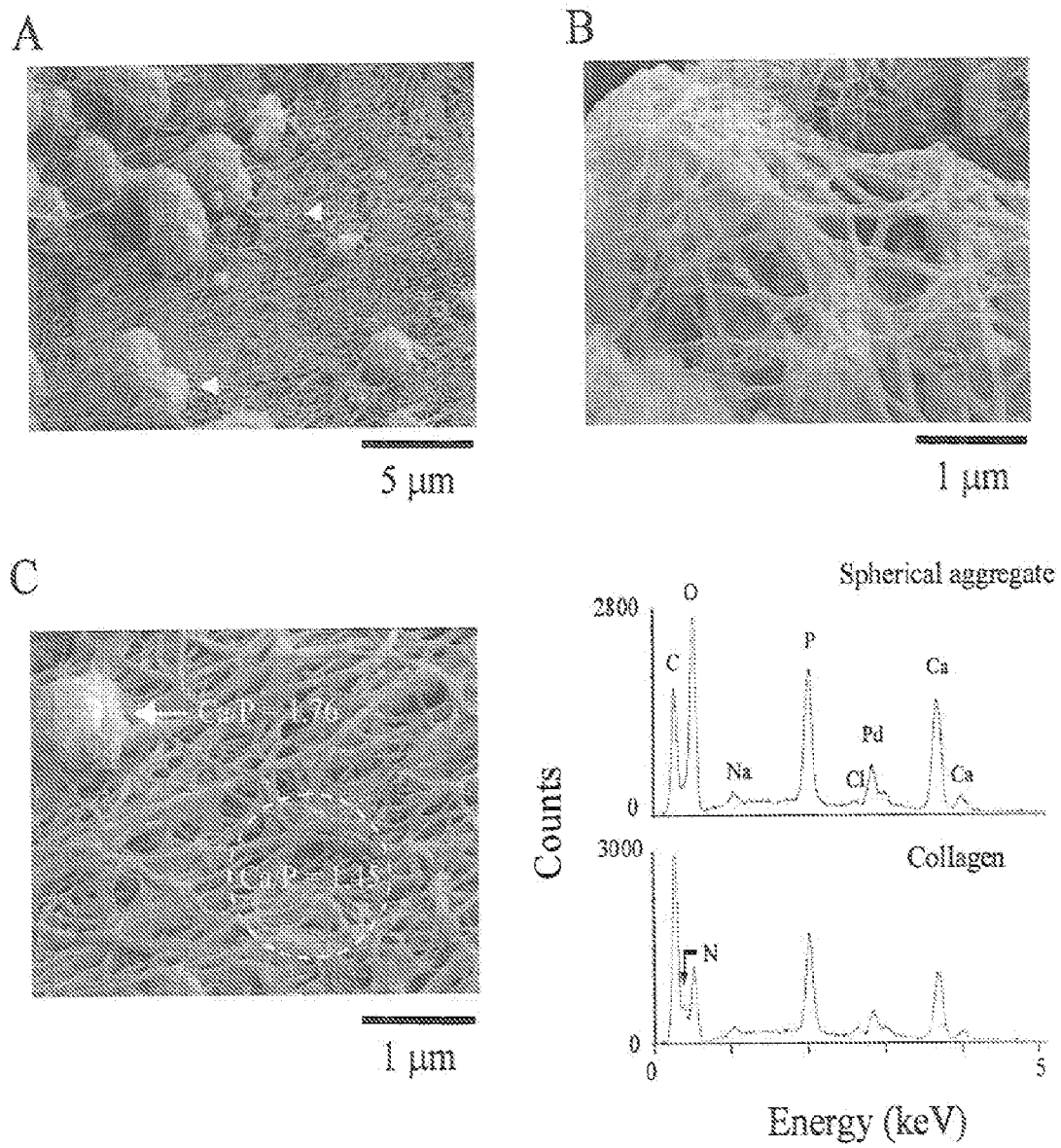
FIG. 5 illustrates SEM images of mineralized collagen fibrils. (A) Large aggregates are associated with the mineralized collagen fibril surface; (B) and these aggregates show a plate-like crystal habit and seem to be trapped by the entangled collagen fibrils. (C) EDX confirmed the Ca—P nature of the spherical aggregate (indicated by arrow). Other elements, including C, O, Na, P, Cl and Pd, are also detected. At the region with no discernable aggregate on the surface (dotted circle), strong Ca—P signal is also detected. In addition to those elements detected in the spherical aggregate, nitrogen (N) peak is also seen.

SEM images show roughly spherical structures associated with the collagen fibrils (a few indicated by arrows in FIG. 5a. These structures appear to consist of aggregates of many plate-like structures with the individual plates being about 100 nm in thickness and several hundred nanometers in length and width. Sizes of the aggregates vary from several hundred nanometers to several microns. These plate-like aggregates seem to be entangled within the collagen fibrils (FIG. 5b).

EDX (FIG. 5c and corresponding EDX spectrum) confirmed the mineral nature of these aggregates showing the presence of calcium and phosphorus at a ratio of about 1.76. This is consistent with these mineral objects being apatitic, indicated by arrow in FIG. 5c. Besides calcium (Ca) and phosphorous (P), sodium (Na), chloride (Cl), carbon (c), oxygen (O) and palladium (Pd) peaks are also present in the EDX spectrum of the spherical aggregate. Detection of Na and Cl peaks are possibly due to their elemental incorporation of the crystal structure of synthetic apatites, which is also observed in bone mineralites. No nitrogen (N) peak is discernible in the EDX spectrum, indicating that most of the C and O signals come directly from the spherical aggregate (If C and O come from collagen, a nitrogen peak should be present.) The Pd peak is due to the conductive coating on the sample surface.

Interestingly, EDX analysis of regions containing none of the spherical structures discussed above also showed calcium and phosphate signals with Ca/P ratio of about 1.45. This indicates the presence of a Ca—P phase within or on the collagen fibrils (region within the dotted white line in FIG. 5c See the corresponding EDX spectrum). Here, the N peak is clearly revealed, presumably due to N in the amino acids of collagen molecules. If nanoapatites similar to those measured previously do exist in our material, they would not be visible by SEM imaging. To test for the presence of these very small mineralites, we used X-ray diffraction and atomic force microscopy to analyze the hydrazine extracted mineralites from our material.

Characterization of Hydrazine Extracted Synthetic Apatites by XRD and AFM

Figure 6:
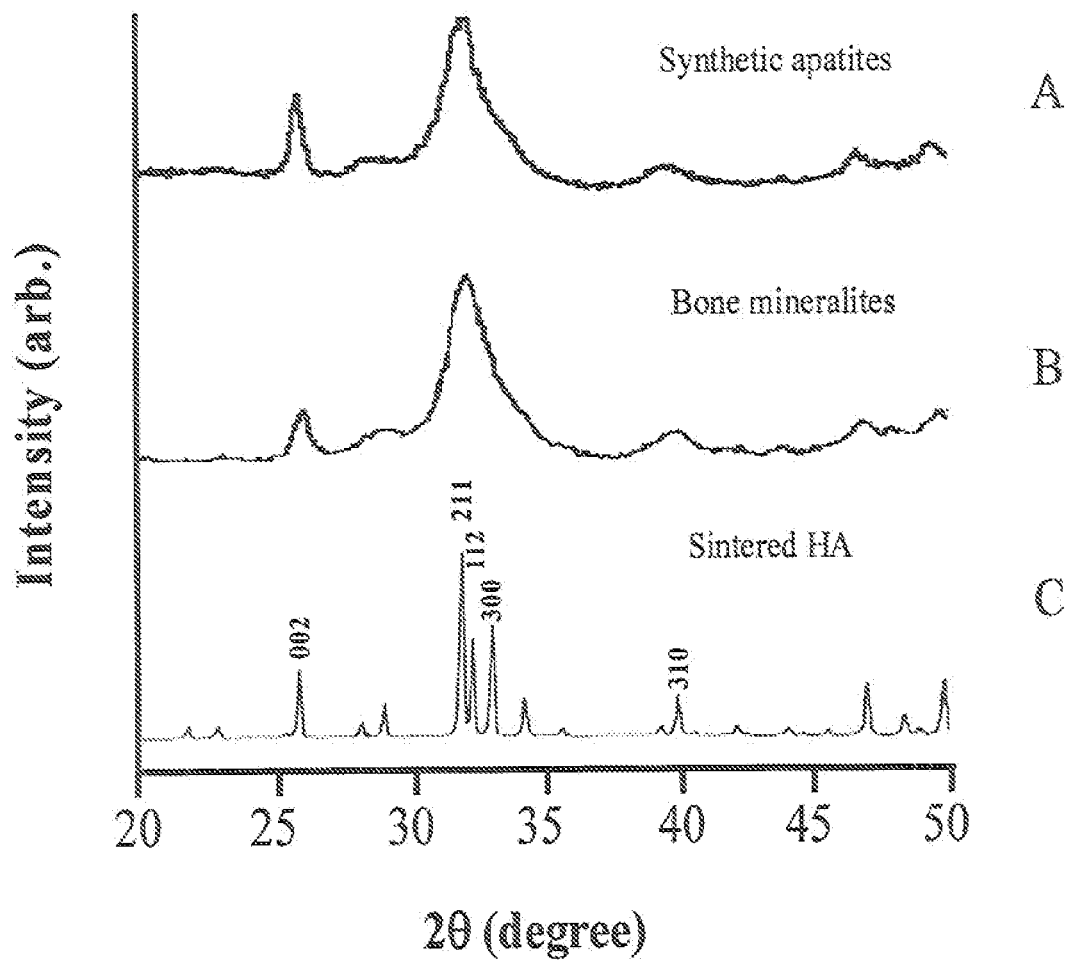
FIG. 6 illustrates X-ray diffraction (XRD) patterns of synthetic apatites (A), native bone mineralites (1-3 week old bovine bone) (B) and sintered HA (G). Synthetic apatites show similar diffraction peaks like native bone mineralites. No triplet peaks are observed in the XRD patterns of synthetic and native mineralites between 30.5° and 33.5° (2θ). Sintered HA exhibits sharp diffraction peaks (narrow peak broadening), with distinctive triplet peaks corresponding to 211, 112 and 300 planes of the HA crystal.

FIG. 6a shows the XRD patterns of hydrazine extracted synthetic apatites. No triplet peaks (211, 112, 300) were observed in the range of 30.5° and 33.5° (2θ) by x-ray diffraction, as would normally be seen in highly crystalline carbonated apatite (FIG. 6c). FIG. 6b is the XRD pattern of the native bone mineralites (1-3 month old bovine cortical bone mineralites). Significant peak broadening can be seen, both in the synthetic apatite and native bone mineralite, while highly crystalline HA exhibits minimal peak broadening most of which originated from instrumental broadening.

Figure 7:
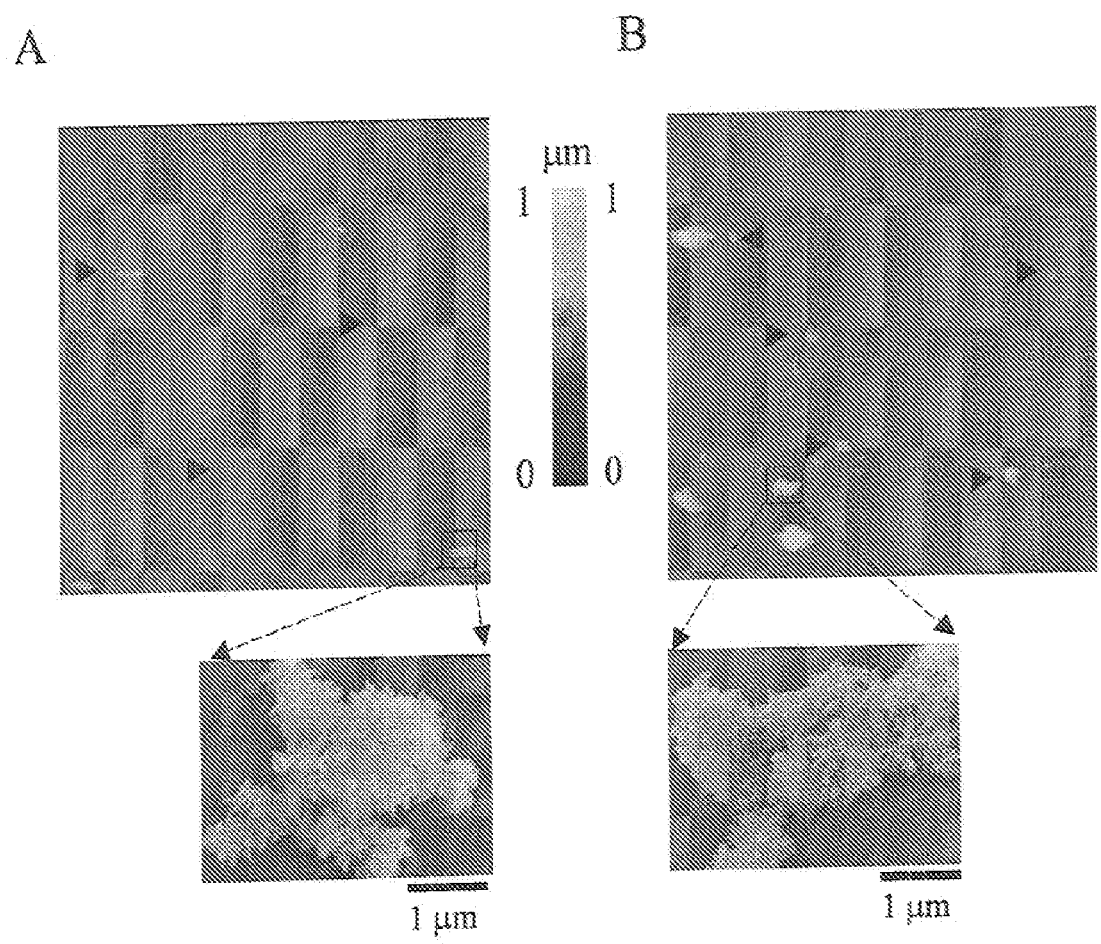
FIG. 7 illustrates 40 µm×40 µm AFM images of: (A) synthetic apatites (138 µg/ml), and (B) control sample (156 µg/ml). Large objects up to several hundred nanometers tall were found on the mica surfaces of both samples (a few indicated by blue arrow heads). Insets of both AFM images are the corroborative SEM studies, showing plate-like aggregates deposited on cover-glass. Note: the SEM images are not actually of the black boxed region, but are indicative of typical features of the sizes seen in the AFM images

FIG. 7a is a 40 μm×40 μm AFM Image of the synthetic apatites on mica surface. The z-range of the image is from 0 to 1 μm. Features several hundred nanometers tall are observed (a few indicated by blue arrow heads on FIG. 7-8a). Corroborative SEM Images (inset of FIG. 7a) show the large apatites are plate-like aggregates, similar to the apatites imaged on collagen fibril surfaces. Similar plate-like aggregates are also seen in the control sample (FIG. 7b) indicating that features of this type do not require collagen fibrils for their production. By decreasing the Z-range to 10 nm and the X-Y range to 10 μm×10 μm, a large number of much smaller features were observed. Control samples do not show these features.

Measurement of features in the AFM images shows that 99.8% of all the features are the small features seen only in the higher resolution images. Measuring a few hundred of these small features shows them to be about 10 nm in length and about 2.5 nm in thickness. This is consistent with the size of an object that would easily fit within the gap zone of the Hodge-Petruska D-staggered array.

Gross Material Characteristics

Figure 8:
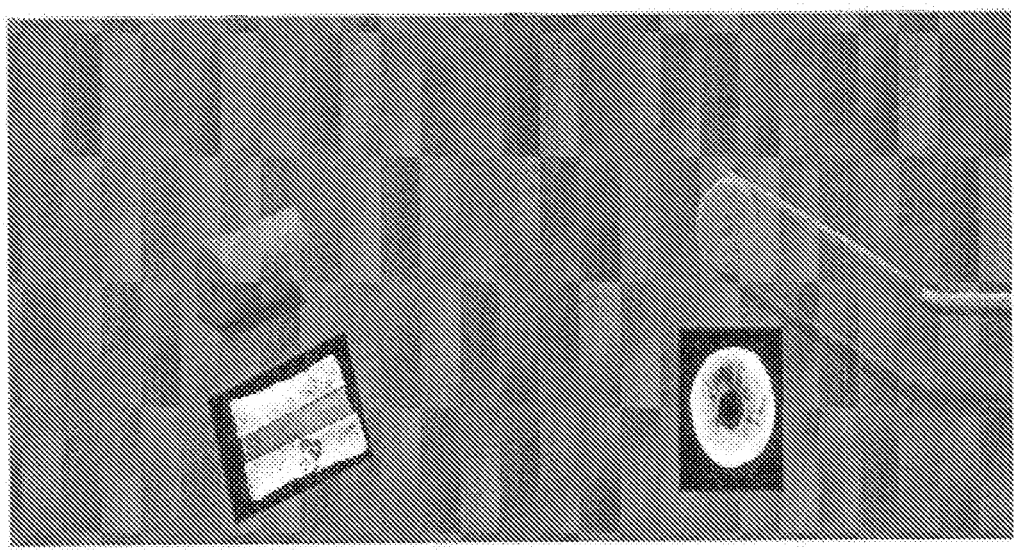
FIG. 8 illustrates oblique and cross sectional views of the actual material after a #60 hole was created by turning the piece on a lathe. Below are µCT images displayed with the same contrast settings used to visualize rat bone thus demonstrating effective mineralization

After completion of the pressing step, a material had grossly strong mechanical properties. It was not at all friable and could be easily machined by gripping it in a lathe and drilling a hole through the long axis of the implant (FIG. 8).

Cytocompatibility Studies

Figure 9:
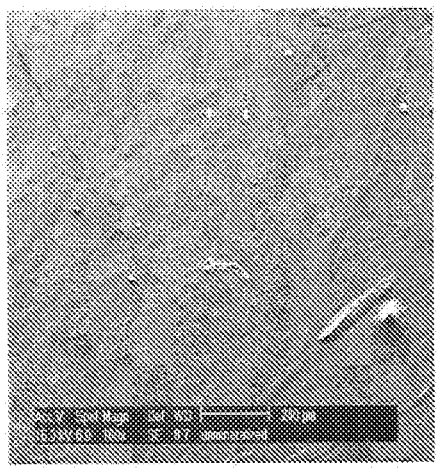
FIG. 9 illustrates an SEM image of the nanocomposite (A), the nanocomposite seeded with cells and a differentiated osteoclast-like cell in the yellow box after it has created a resorption pit (B), and a magnified image of the resorption pit (C).
Figure 9:
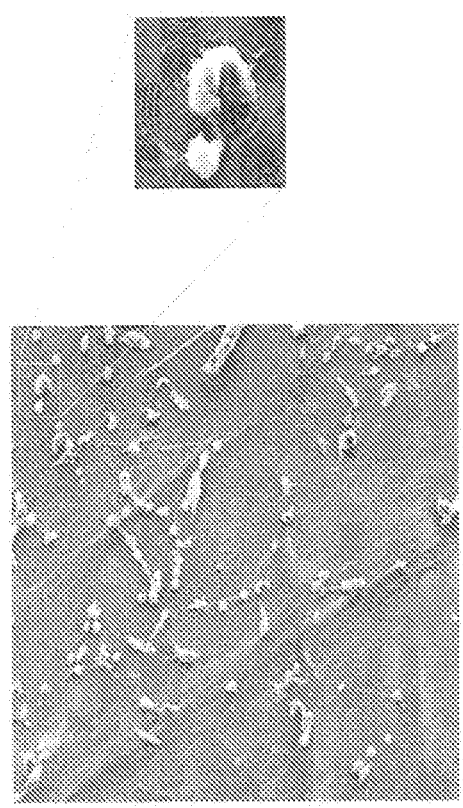

To test the cytocompatibility of our material with osteoblast-like cells, we seeded ST2 cells onto our material. These cells robustly adhered, spread and proliferated on the surfaces growing to confluence in a matter of days. Using primary cell isolates from fetal mouse spleens, along with dexamethasone and ascorbic acid, we were able to get the stem cells to differentiate along the osteoclast cell line and obtain mature, active, multinuclear osteoclasts. These cells stained robustly with tartrate resistant acid phosphates and were found to produce resorption-like pits on our material surface as determined by SEM imaging (FIG. 9). To compare our material with unmineralized collagen gels and sintered hydroxyapatite, we determined the number of resorption events visible on a surface and normalized this to the number of osteoclasts present on the surface. A resorption event was defined to be an SEM visible depression in the surface which showed a visible boundary around at least 75% of the depressions perimeter. In addition, the roughness of the surface within the depression as determined by the standard deviation of gray values in the SEM image had to be at least 1.4× larger than the standard deviation on an equal sized region measured just outside the perimeter of the event. Using this analysis, we found the number of resorption features per cell was twice as high on the nanocomposite as it was on the unmineralized collagen fibrils or the sintered HA.

With the results in hand that we had physico-chemically duplicated much of the submicron chemistry and architecture of bone and the cell studies indicating our material was cytocompatible and appeared to elicit an osteoclast mediated resorption response, we set out to perform an animal pilot study.

Pilot Study

The nanocomposite demonstrated more compressibility in the aqueous in-vivo environment than it did in a non-aqueous environment. However, both the control and experimental animals recovered quickly after the surgery and were back to a normal diet within a week. There did not appear to be any significant difference between the control or experimental animals in terms of weight fluctuation or ability to eat solid food.

Figure 10:
FIG. 10 illustrates explanted mandible (dissected free of soft tissue) of a control animal (no implantation) at the conclusion of an 8 week study. On the left is a left hemimandible following the creation of an unimplanted critical size defect (arrow). On the right is the unoperated contra-lateral side.
Figure 11:
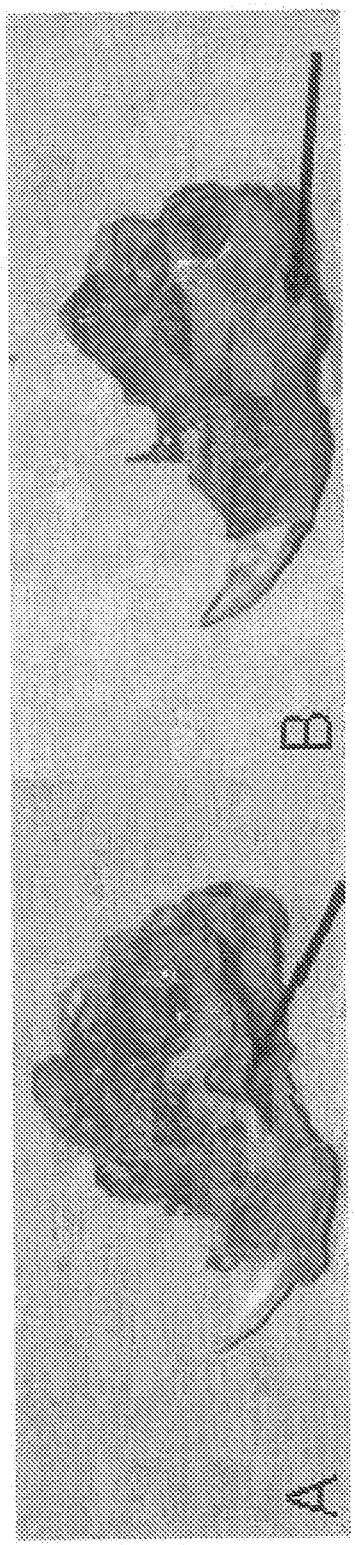
FIG. 11 illustrates explanted left hemimandibles (with soft tissue attached) in the experimental groups at the conclusion of the 8 week study. (A) Undoped nanophase composite implanted in the critical size defect arrow and (B) BMP2 doped nanocomposite implanted in a critical size defect with robust bony ingrowth (arrow).

The defect in the unimplanted animals was minimally changed after 8 weeks. This demonstrated that the defect created was in fact a critical size defect (FIG. 10). There was some remodeling at the edges of the defect but little change in the overall dimensions of the defect. There was no evidence of any remaining implant material in any of the implanted animals. The animals with the collagen sponge implanted showed little change in defect dimensions with no bony response. There was no gross inflammation noted in this group. The rats with the nanocomposite implanted had a greater degree of closing of the defect than the controls but there was not complete spanning of the defect with new bone. There was no gross inflammation noted in this group. The rhBMP2 doped nanocomposite group demonstrated complete bony healing with spanning of the entire defect with what grossly appeared to be cortical bone (FIG. 11). There was no gross inflammation in this group as well.

Mechanical Testing Results

The ratios of operated to unoperated mechanical properties are presented in Table 1. The unoperated hemi-mandibles were able to withstand greater load than the operated mandibles (40.8N vs 80.8N, p<0.05). When expressed as a ratio of operated to unoperated hemimandible the 2 rats with rhBMP2 doped implants withstood the greatest load and had the greatest stiffness relative to both those with undoped implants and those with no implants. The trend was for animals with non-doped implants to have better mechanical properties than those that had not been implanted at all.

TABLE 1

Ratios of Operated to Unoperated Mechanical Properties

| Implant Type | Load % | Stiffness % |
|---|---|---|
| Control | 25 | 67 |
| Control | 20 | 17 |
| Implant with no BMP | 61 | 105 |
| Implant with no BMP | 42 | 73 |
| Implant with BMP | 87 | 111 |
| Implant with BMP | 63 | 100 |

The data represents the ratios expressed as a %. Note the increasing load necessary to produce failure when comparing the control to the undoped nanocomposite and to the doped nanocomposite. Stiffness is increased in both experimental groups when compared to the controls.

There are several synthetic bone substitute products available to the surgeon for reconstitution of bony defects. They generally fail to meet the functional requirements of bone because they do not replicate the biology, chemistry, and/or architecture of bone. Bone is a complex nanocomposite consisting of an organic phase—which can be further broken down into a fibrillar or collagenous matrix and a non-fibrillar protein matrix—and an inorganic phase. The inorganic or mineral component of bone is generally agreed to take the form of an apatitic mineral structure. The mineral has also been fairly well established to be carbonated apatite where a phosphate anion is substituted for a carbonate. It has been shown that a structurally biomimetic bone substitute needs to contain apatitic mineralites that are about 1 nm×10 nm×10 nm. Two technological problems exist in meeting this design constraint. First, it is difficult to synthesize such small mineralites. Second, implantation of a powder this size would result in migration of the material away from the implant site. Nature has solved both of these problems by templating mineralization using collagen fibrils. The nanoscale voids within a self-assembled native collagen fibril limit the size to which the mineralites can easily grow. In addition, the formed mineralites are entrapped within the collagen fibrils so they do not diffuse away. In this way bone becomes both structurally stiff and chemically accessible to the remodeling activities of osteoclasts.

Through the process herein described nanometer-sized carbonated apatitic crystals were created using a native-type collagen fibrils. The sizes and shapes of the synthetic carbonated apatites mimic biologically derived bone mineralites. The average size and shape of the synthetic nanoapatites agree with the size and shape of native bone mineralites within one standard deviation. There are other reports in the literature of similar composite materials in development. One research group made a mineralized collagen material in which they synthesized collagen fibrils and mineralized them simultaneously. They pressed the material to form clinically useful shapes with strength and moduli similar to trabecular bone. Studies in beagles showed dogs were able to bear weight on critical size full thickness lower limb defects filled with the material two weeks after implantation. Our material differs from the previously studied material in that we are careful to form native collagen fibrils prior to mineralization. This is the way bone is formed naturally and it ensures that the size and distribution of the mineralites within the collagen fibrils is biomimetic.

Using a cell culture assay, we found that the nanocomposite described here supports adhesion and division of osteoblast like cells. We also found hematopoeitic stem cells can be enticed to differentiate into osteoclasts on the material. These osteoclasts formed resorption pits visible after two weeks of cell culture. Osteoclast resorption activity was highest on the nanocomposite which had at least twice as many resorption pits as either collagen fibrils or sintered HA alone.

The nanocomposite, once uniaxially pressed, is strong enough to machine in a lathe though it is not as strong or tough as cortical bone. One feature noted in the material characteristics during implantation was an apparent increase in compressibility in the aqueous in-vivo environment relative to the dry state. However, there was no clinical manifestation of implant failure based on animal behavior or the characteristics of the mandible upon explanation. Most notable in the pilot study was the bony response to the rhBMP2 doped implant. rhBMP2, a member of the TGFβ family, is well known to be highly osteoinductive and has gained wide clinical acceptance in medicine. In this study, when doped with rhBMP2 the material produced complete spanning of the defect with grossly normal appearing cortical bone. This demonstrates that the material appears to function well as a carrier for rhBMP2 and possibly for other bioactive molecules as well.

When mechanically tested there was a significant decrease in the mechanical properties of the mandible after creation of a defect. This is most notable in the maximum load that the mandibles were able to withstand before fracture. As seen in Table 1, the maximum load of all mandibles decreased after defect creation. This is important because it demonstrates that implants were in fact bearing a load. Not surprisingly, the control mandibles had the largest decrease in maximum load, with the mandibles fracturing at around 20% of the maximum load of the unoperated mandibles. In implanted mandibles the decrease in maximum load was less pronounced. Rats that received an implant without $BMP_2$ fractured at around 40-60% of the unoperated load, while rats that received a $BMP_2$-doped implant fractured at around 60-90% of the unoperated load.

Similar results were seen when comparing the stiffness of the operated and unoperated mandibles. Again, the control mandibles demonstrated the largest decrease in stiffness as a function of defect creation although there was a large variability between the 2 animals. The experimental animals demonstrated no significant change in stiffness after surgery and implantation. Little difference was observed between the two experimental groups with respect to stiffness.

The results presented here support several conclusions about this nanocomposite bone substitute. The material appears to be osteoinductive and with rhBMP2 osseoinductive allowing bony growth in a relatively short time span. It supports osteoclastic remodeling in-vitro and appears to do so in-vivo as well though this is clearly needs to be studied on a larger scale. Larger animal studies with careful histological analysis will be necessary to fully evaluate the biological response to the implant. However, grossly the material does not behave like a foreign body and after 8 weeks is entirely resorbed. The results with rhBMP2 were very encouraging and suggest that the nanocomposite has promise as a highly effective carrier of rhBMP2 specifically and bioactive molecules in general. Studies are underway to evaluate a method for sterically interdigitating bioactive molecules within fibrils. This approach would enable a slow diffusion of the molecule into the extracellular milieu as the implant is resorbed. This would extend the activity of the bioactive agent. It could also reduce to quantity of the bioactive molecule needed which would dramatically cut down on the cost of the implant.

The material described here has strong potential as a load bearing bone substitute. It is not as strong as cortical bone but the mechanical properties are being further enhanced. Several strategies are being employed to achieve this objective. Biological bone undergoes increasing mineralization during development. The material described here appears to be undermineralized relative to native bone which results in a weaker substrate. Methods are being sought to increase intrafibrillar mineralization. Another important area of research is the role of the non-collagenous protein matrix. This matrix is theorized to play an important role in the mechanical properties of bone. Techniques are being investigated to increase intra- and extra-fibrillar bonds. Finally, the type of mechanical dehydration can also be altered to effect a greater degree of strength and toughness. This last step, however, has to be carefully balanced against the reduction in porosity that is inevitable with increased material density.

CONCLUSIONS

A novel nanocomposite biomaterial is described which was designed specifically to function as a load bearing bone substitute. Physico-chemical characterization has demonstrated that the material is chemically and architecturally biomimetic on a nanoscale. In-vitro cytocompatibility studies showed that the nanocomposite supports osteoclastic differentiation and resorption. A pilot study using a critical size defect in the rat mandible has established proof of concept that this nanocomposite, when doped with rhBMP2, has promise as a load bearing bone substitute. It is resorbed via the bone remodeling cycle and replaced by normal bone.

From the above description of the invention, those skilled in the art will appreciate improvements, changes, and modifications. Such improvements, changes and modifications are intended to be covered by the appended claims.

Having described the invention the following is claimed:

1. A biomaterial implant comprising:
a mineralized collagen fibril scaffold including nanoscale mineralite that is interdigitated within the collagen fibrils of the scaffold, the collagen fibrils being formed from collagen monomers, displaying native-D banding periodicity, the collagen fibrils having an average diameter of about 30 nm to about 130 nm, and defining a plurality of gaps in the scaffold, the gaps having an average volume of about 50 $nm^3$ to about 250 $nm^3$, the nanoscale mineralite having a calcium to phosphate ratio (Ca/P) of about 1.4 to about 1.8, the implant having load bearing capabilities and being replaced with native bone via the normal bone remodeling when implanted in a mammal's body.

2. The biomaterial implant of claim 1 being osteoconductive and resistant to hydrolysis when implanted in a mammal.

3. The biomaterial implant of claim 1, the nanoscale mineralite including at least one of calcium phosphate based mineralite, apatitic mineralite, carbonated apatite, or substituted carbonated apatite.

4. The biomaterial implant of claim 3, the mineralite comprising crystalline carbonated apatite.

5. The biomaterial implant of claim 3, the mineralite having an average particle size of about 25 $nm^3$ to about 150 $nm^3$.

6. The biomaterial implant of claim 1 having a dry modulus of about 500 MPa to about 20 GPa.

7. The biomaterial implant of claim 1, further comprising at least one of bioactive molecule, growth factor, or bone morphogenic protein interdigitated between collagen molecules within collagen fibrils.

8. The biomaterial implant of claim 1, the mineralized collagen fibril scaffold being at least partially cross-linked with a cross-linking agent.

9. The biomaterial implant of claim 1, wherein the mineralized collagen fibril scaffold is isostatically pressed.

10. A method of treating a bone injury or defect in a subject, comprising:

administering to the injury or defect of the subject a biomaterial implant, the biomaterial implant including a mineralized collagen fibril scaffold including nanoscale mineralite that is interdigitated within the collagen fibrils of the scaffold, the collagen fibrils being formed from collagen monomers, displaying native-D banding periodicity, the collagen fibrils having an average diameter of about 30 nm to about 130 nm, and defining a plurality of gaps in the scaffold, the gaps having an average volume of about 50 nm$^3$ to about 250 nm$^3$, the nanoscale mineralite having a calcium to phosphate ratio (Ca/P) of about 1.4 to about 1.8, the implant having load bearing capabilities and being replaced with native bone via the normal bone remodeling when administered to the injury or defect.

11. The method of claim 10, the injury or defect comprising at least one of a craniomaxillofacial injury or defect, a spine injury or defect, an appendicular injury or defect, or a pan-skeletal injury or defect.

12. The method of claim 11, further comprising shaping the biomaterial implant with presses that are preshaped to the particular injury or defect prior to implantation.

13. The method of claim 11, further comprising machining the biomaterial implant prior to administration.

14. The method of claim 11, the nanoscale mineralite including at least one of calcium phosphate based mineralite, apatitic mineralite, carbonated apatite, or substituted carbonated apatite.

15. The method of claim 11, the biomaterial implant further comprising at least one of bioactive molecule, growth factor, or bone morphogenic protein.

16. The method of claim 11, the mineralized collagen fibril scaffold being at least partially cross-linked with a cross-linking agent.

17. The method of claim 10, wherein the mineralized collagen fibril scaffold is isostatically pressed.

* * * * *